United States Patent
Welin

(10) Patent No.: US 9,168,905 B2
(45) Date of Patent: Oct. 27, 2015

(54) SENSOR UNIT FOR A DISC BRAKE

(71) Applicant: Hans Welin, Sankt Ibb (SE)

(72) Inventor: Hans Welin, Sankt Ibb (SE)

(73) Assignee: Haldex Brake Products AB (SE)

( * ) Notice: Subject to any disclaimer, the term of this patent is extended or adjusted under 35 U.S.C. 154(b) by 248 days.

(21) Appl. No.: 13/621,442

(22) Filed: Sep. 17, 2012

(65) Prior Publication Data
US 2013/0068571 A1    Mar. 21, 2013

Related U.S. Application Data

(63) Continuation of application No. PCT/EP2011/001208, filed on Mar. 11, 2011.

(30) Foreign Application Priority Data

Mar. 17, 2010 (DE) .................... 20 2010 003 737 U

(51) Int. Cl.
F16D 66/02 (2006.01)
B60T 17/22 (2006.01)
G01L 5/28 (2006.01)
G01N 3/56 (2006.01)

(52) U.S. Cl.
CPC ............... *B60T 17/22* (2013.01); *F16D 66/027* (2013.01); *G01L 5/28* (2013.01); *G01N 3/56* (2013.01)

(58) Field of Classification Search
CPC ..... F16D 66/024; F16D 66/02; F16D 66/021; F16D 66/026; F16D 66/027; B60T 17/22; G01L 5/28; G01N 3/56

USPC ......... 188/1.11 L, 1.11 E, 1.11 W, 71.7–71.9, 188/72.1, 72.7–72.9; 340/454; 116/208

See application file for complete search history.

(56) References Cited

U.S. PATENT DOCUMENTS

| 3,887,040 | A | * | 6/1975 | Simon et al. ............. | 188/1.11 R |
| 5,632,359 | A | * | 5/1997 | Camps et al. ............ | 188/1.11 R |
| 5,848,673 | A | * | 12/1998 | Strauss et al. ............ | 188/1.11 L |
| 6,276,494 | B1 | * | 8/2001 | Ward et al. ............... | 188/1.11 W |
| 7,322,447 | B2 | * | 1/2008 | Deckhut et al. .......... | 188/1.11 L |
| 8,464,842 | B2 | * | 6/2013 | Cahill ....................... | 188/1.11 L |
| 8,717,159 | B2 | * | 5/2014 | Todd et al. ................ | 340/454 |
| 2008/0073161 | A1 | * | 3/2008 | Pettersson et al. ....... | 188/1.11 L |

FOREIGN PATENT DOCUMENTS

| DE | EP-0492143 A1 * | 7/1992 |
| DE | EP-0566006 A1 * | 7/1992 |
| DE | EP-0784162 A2 * | 7/1997 |
| IT | EP-1069336 A1 * | 1/2001 |
| WO | WO-2004/111484 A1 * | 12/2004 |

* cited by examiner

*Primary Examiner* — Pamela Rodriguez
(74) *Attorney, Agent, or Firm* — St. Onge Steward Johnston & Reens LLC

(57) ABSTRACT

A sensor device for the detection of the lining wear at a disc brake having a brake caliper and a brake actuation mechanism being arranged in the brake caliper, which includes a thrust piece which cooperates directly or indirectly with a brake lining so that a movement of the brake lining corresponds to the movement of the thrust piece, in which the sensor device can be inserted as a unit into the housing of the brake caliper from the rear.

12 Claims, 3 Drawing Sheets

SENSOR UNIT FOR A DISC BRAKE

FIELD OF THE INVENTION

The present invention relates to a sensor unit for determining the wear of brake linings of a disc brake, in particular for an utility vehicle.

BACKGROUND OF THE INVENTION

In the field of disc brakes sensor units for wear detection with different embodiments are known.

From EP 0 492 143, for example, it is known to detect the wear of the brake linings at the end of an adjustment spindle facing away from the brake disc, in that the rotation of the adjustment spindle, which correlates with the translational movement compensating the wear-induced clearance or slack, is utilized as a measure. A similar method has been described in EP 0 566 006.

DE 43 12 377 discloses a sensor device in which the displacement movement of the brake actuation mechanism in the brake caliper is preferably detected by a linear potentiometer.

From EP 0 784 162 a wear monitoring device is known in which the movement of a thrust spindle is detected by means of a gear. For that purpose the thrust spindle comprises a gear rack which meshes with a gear pinion of a sensor unit.

From WO 2004/111484 of the applicant it is known to linearly sense the movement of the thrust spindle at the face surface of the thrust spindle facing away from brake disc.

It is common to all solutions of the prior art that these cannot ensure an exact wear sensing, since always the tolerances in the brake actuation mechanism and vibrations and tensions in the brake caliper do influence the measuring result and thus do negatively affect the accuracy.

SUMMARY OF THE INVENTION

Starting from the disadvantages known from the prior art it is an object of the invention to provide a sensor unit for determining the lining wear, which determination is substantially de-coupled from the negative influences from the surroundings of the brake caliper.

Furthermore, it is an object of the invention to provide a sensor unit which can be easily assembled and disassembled.

These objects, respectively, are solved with a sensor device according to claim 1.

The sensor device according to the invention can be utilized both in disc brakes with sliding calipers and in disc brakes with fixed calipers.

Thus, the core of the invention is that the sensor device for the lining wear does indirectly or directly interact with the thrust piece, in which the sensor device can be inserted as an unit into the housing of the brake caliper from the rear and freely passes the housing of the brake caliper up to the thrust piece, in particular in parallel to the axis of the brake disc.

The thrust piece is part of the brake actuation mechanism which, independent of its configuration, directly attaches to the brake lining and its brake pad, respectively. The thrust piece is linearly adjusted by means of an adjustment device in order to compensate the wear-induced slack between the brake lining and the brake disc.

The sensor device is formed as a module which can be exchanged as a whole. For that purpose a corresponding receiving or fixture opening is provided in the housing of the brake caliper into which the sensor device can be sealingly inserted and fastened.

The sensor device comprises a transmitting element for transmitting the linear movement of the thrust piece into a rotational movement and a sensor element for detecting the rotational movement.

The transmitting element is formed as a sleeve attaching to the thrust piece, which sleeve is arranged in displaceable manner relative to a stationary, but rotatably supported threaded element. The sleeve is in engagement with the threaded element such that upon displacement of the sleeve, together with the linear movement of the thrust piece, the threaded element is set into rotation. At its end facing away from the brake disc the threaded element cooperates with at least one sensor element in a touchless manner.

Since the threaded element only rotates, the sensor element detects the rotational movement which will be computed into the actual existing wear by means of a corresponding calculation circuit of the sensor element, which wear results from the linear adjustment movement, which is performed by the thrust piece.

Preferably the at least one sensor element is formed as a Hall-sensor and interacts in a known manner with at least one magnet being arranged at the end of the threaded element facing away from the brake disc.

In order to facilitate the detection of the wear in one preferred embodiment, the thread pitch of the threaded element is selected such that at most one entire rotational movement will be performed by the threaded element for the entire possible linear displacement of the sleeve. By that the calculation circuit can be simplified, since not more than one turn corresponding to a maximum possible wear has to be associated.

In order to always ensure a perfect contact of the sleeve with the thrust piece, in particular with respect to the vibrational and rocking loads existing in the brake surroundings, the sleeve is biased in axial direction. A spring surrounding the threaded element is supported between a rear housing section of the sensor device and the sleeve.

Basically, the invention is characterized by the advantage that only very few fixation means are required for the assembly of the sensor unit and its fixation in the brake caliper.

Moreover, the relative movement of the thrust piece and thereby of the brake lining will be directly sensed so that both further components of the brake actuation mechanism and of the brake caliper themselves cannot influence the measuring result.

BRIEF DESCRIPTION OF THE DRAWINGS

Further advantages and features of the present invention will become apparent from the embodiment as shown in the attached drawings.

DETAILED DESCRIPTION OF THE INVENTION

Figure 1:
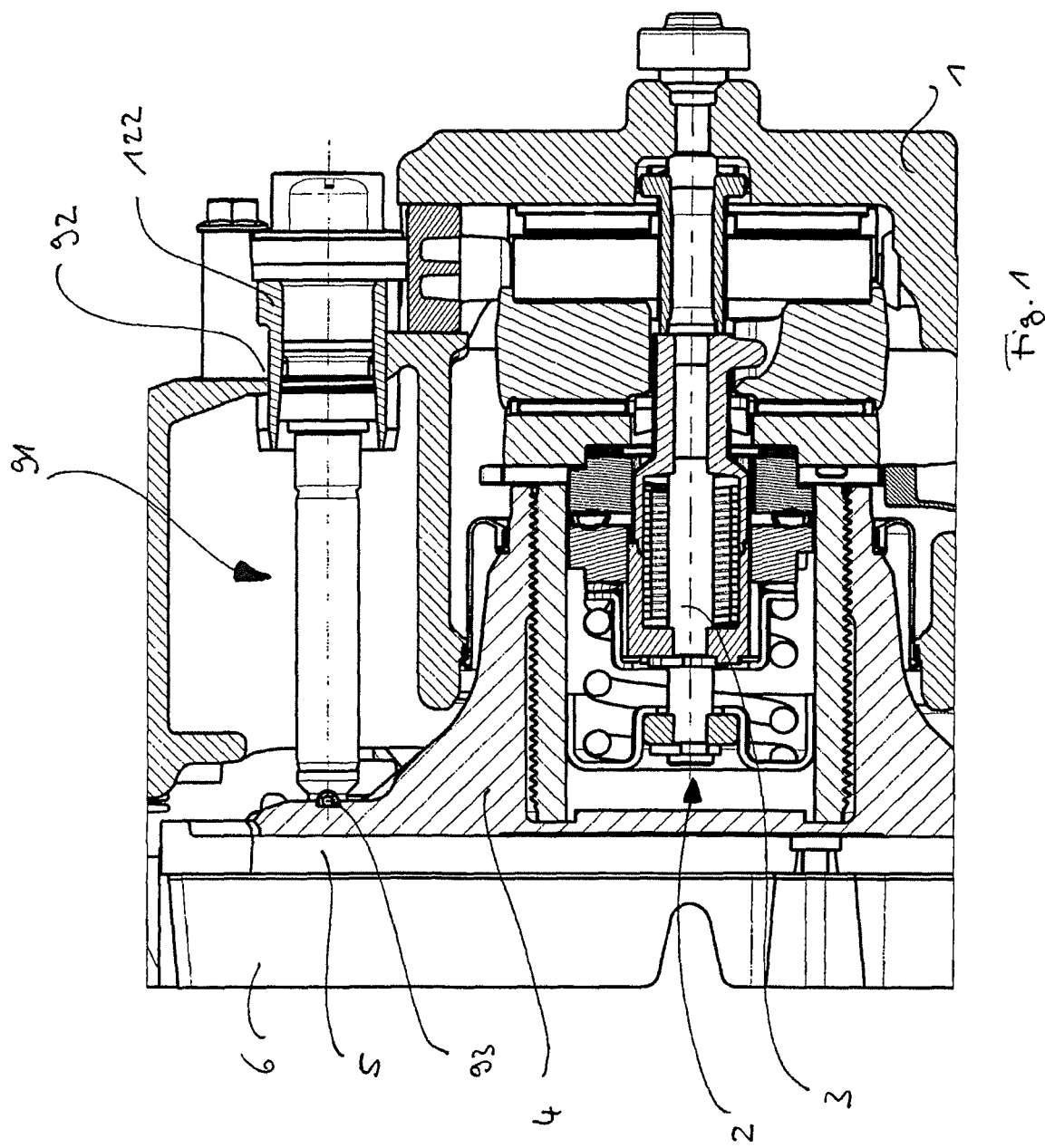
FIG. 1 shows an arrangement of a sensor unit for determining the lining wear according to the invention in a brake caliper of a disc brake.

FIG. 1 shows partly in cross-section a brake caliper 1 of a disc brake from which the arrangement of the sensor unit 91 according to the invention can be recognized.

A brake actuation mechanism 2 is fixed and functionally guided on a central rod 3 in the housing of the brake caliper 1 co-axially to the axis of the brake disc not shown herein.

The brake actuation mechanism 2 comprises a thrust piece 4 which directly cooperates with a brake lining 6 by means of a pad retainer 5. I.e. the translational movement of the brake lining 6, also during the wear adjustment is identical to the displacement movement of the thrust piece 4, since the pad retainer 5 is in fixed connection with the thrust piece 4.

For the purpose of wear adjustment the brake actuation mechanism 2 comprises an adjustment device, the functioning of which shall not be further explained herein.

The sensor unit 91 will be inserted through a receiving or fixture opening 92 into the housing of the brake caliper 1 from the rear. At its end facing the brake disc the sensor unit 91 comprises means 93 for connection with the thrust piece 4, for example an again releasable clamp- or snap-element or a plug-in connection by means of a pin, which cooperates with a corresponding element of the thrust piece 4.

Thus, the sensor unit 91 according to the invention is configured such that it detects the relative movement of the thrust piece 4 in relation to the brake caliper 1 during the adjustment of the clearance.

The sensor unit 91 freely traverses the interior of the brake caliper 1 and in parallel to the axis of the rod 3.

In this connection the sensor unit 91 is guided in the fixture opening 92 in the brake caliper 1 on the one hand and at the opposite side by means of the connection with the thrust piece 4 via the pin element 93 on the other hand, so that a substantially strict axial movability without tilting is realized.

Figure 2:
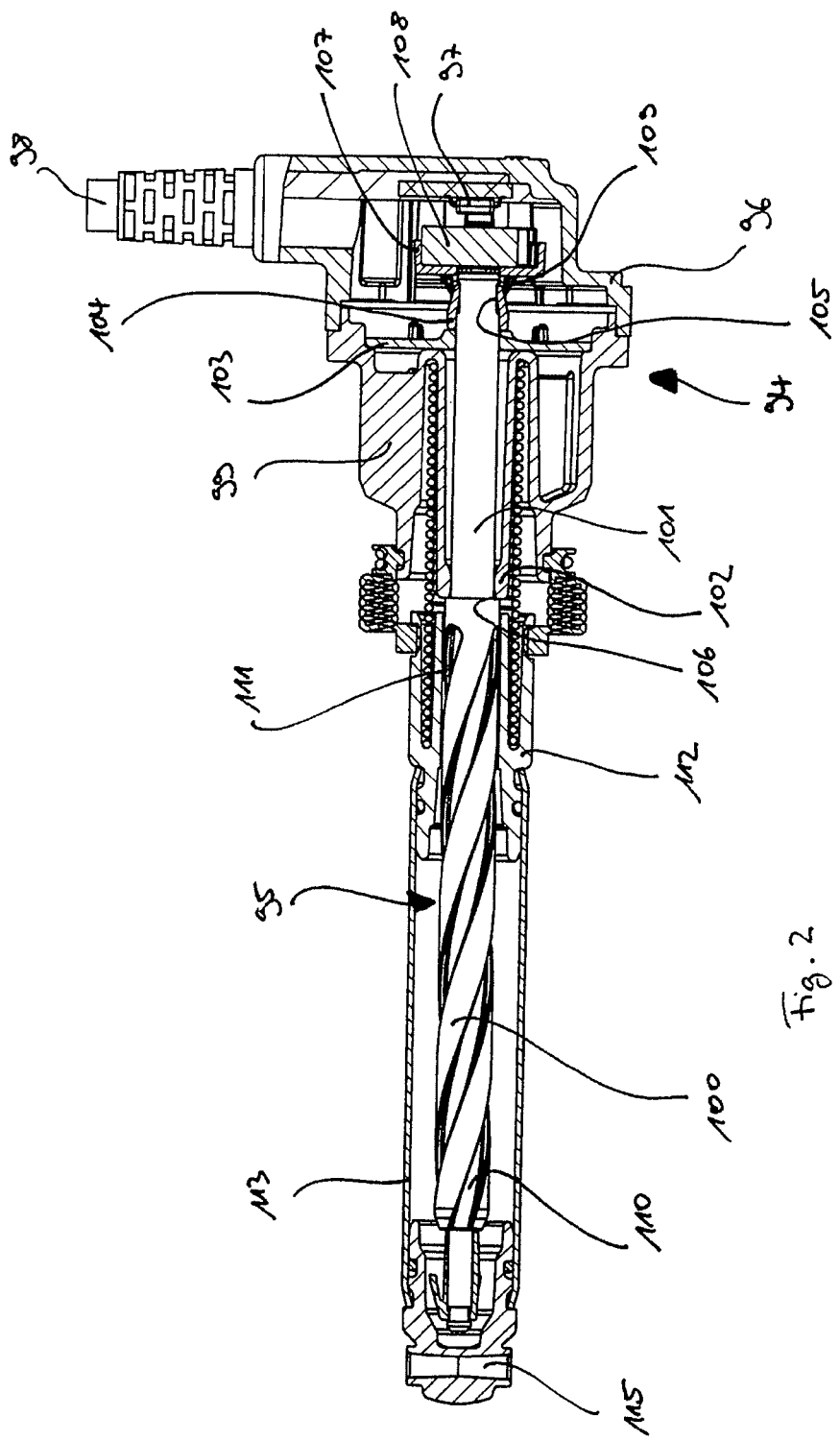
FIG. 2 schematically shows a sensor unit in cross-section in its starting position.
Figure 3:
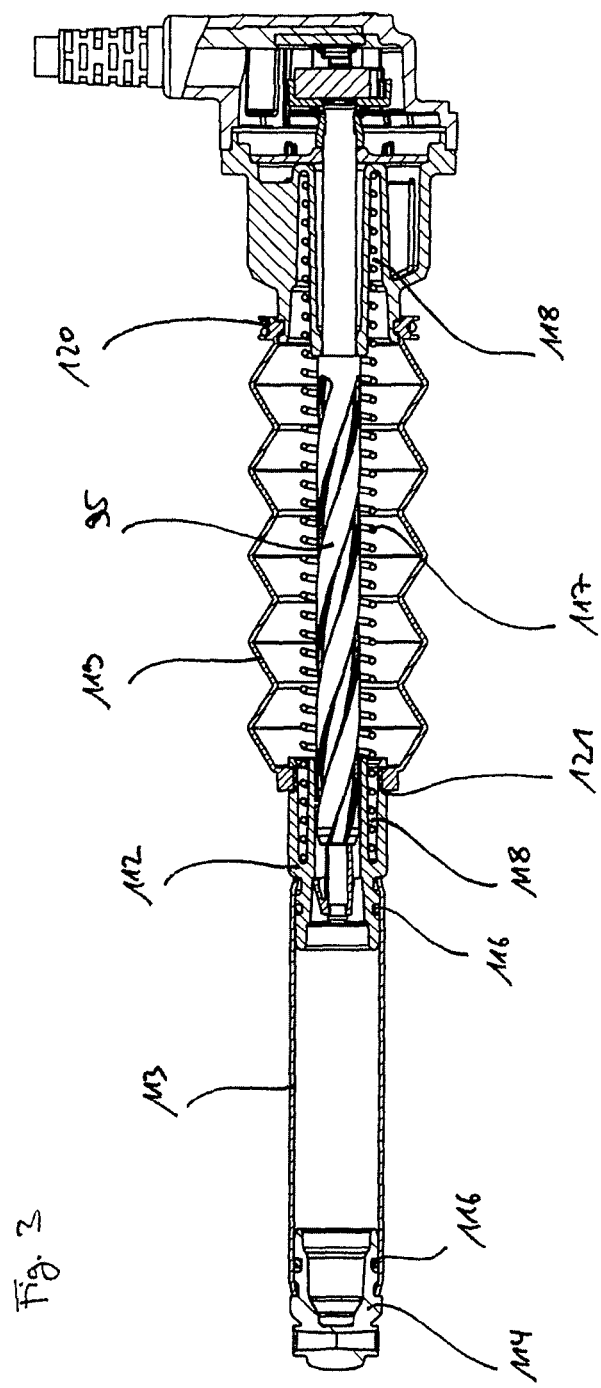
FIG. 3 schematically shows the sensor unit in cross-section in an extended state.

As can be seen in FIGS. 2 and 3 the sensor unit 91 comprises a stationary, rear housing 94, in which a threaded element 95, for example a spindle, is rotatably, but not displaceably guided.

The housing 94 comprises a rear housing fixture 96 which in the mounted state of the sensor unit 91 is located outside of the housing of the brake caliper 1. This housing fixture 96 includes a sensor element 97, which preferably consists of at least one Hall-element. From the housing fixture 96 a connection 98 leads to a boardside computer network in order to be able to conduct the actual wear condition.

The housing fixture 96 is attached onto a housing support part 99 and releasably fixed to it. The sensor unit 91 is fastened in the fixture opening 92 of the brake caliper 1 by means of the housing support part 99.

On the one hand the housing support part 99 serves for the rotatable support of the spindle 95 and on the other hand for the connection of a transmitting element being displaceable relative to it.

The spindle 95 which comprises a threaded section 100 and a cylindrical section 101 is rotatably supported with the latter in a guidance 102 of the housing support part 99. In this connection the spindle 95 is axially fixed between the threaded section 100 and the cylindrical section 101, which abuts against the guidance 102, axially in the direction facing away from the thrust piece 4 by means a shoulder-like transition 106. In the axial direction being directed towards the thrust piece 4 the spindle 95 is axially positioned and fixed by means of a bearing sleeve 104. The bearing sleeve 104 therefore is supported against a cover 103 which is inserted into the housing support part 99. Furthermore, the bearing sleeve 104 engages with a chamfer 105 of the cylindrical section 101 by means of tongues 109.

At the rear end of the bearing sleeve 104 a guiding cup 107 is provided in which at least one magnet 108 is arranged so as to be rotationally fixed with the end of the spindle 95.

The magnet 108 rotates by a distance over the Hall-element of the sensor element 97. Accordingly, it concerns a touchless detection of the wear.

The threaded section 100 of the spindle 95 comprises a thread 110 with a very large pitch. The thread 110 is in engagement with a displacement block 112 by means of a pin element 111.

The displacement block 112 is movable relative to the housing support part 99 and comprises a sleeve 113 into which the threaded section 100 of the spindle 95 does extend. The sleeve 113 terminates in an end housing 114 which comprises an opening 115 for the pin element 93 for connection with the thrust piece 4. The sleeve 113 together with the sealing rings 116 serves for the protection of the threaded section 100 against dirt.

As can be seen from FIGS. 2 and 3 the transmitting unit consisting of the end housing 114, the sleeve 113 and the displacement block 112 is displaced together with the thrust piece 4 in axial direction towards the brake disc or away from it. This displacement movement, from which the adjustment movement for the wear can be derived, will be transformed into a rotational movement of the spindle 95 by means of the coupling with the pin element 111, in which, in turn, the rotation of the spindle 95 resulting therefrom will be detected by the Hall-element 97 by means of the rotating magnets 108 and then computed in a calculation circuit, correspondingly.

According to the invention the pitch of the thread 110 is selected such that the entire possible length of the axial displacement path of the sleeve 113 and of the displacement block 112, respectively, results at most in one complete turn of the spindle 95. I.e. the displacement path for the adjustment, which is possible at most till the brake linings 8 and the brake disc will be completely worn, never exceeds a 360°-rotation of the spindle 95. Thereby the measuring accuracy can be increased by a more simple circuit.

In order to always ensure a perfect contact of the end housing 114 with the thrust piece 4 and in order to always maintain a faultless guidance of the pin element 111 in the thread 110 during the displacement movements of the displacement block 112, the latter is biased in relation to the housing support part 99, which bias is provided by a spring 117 between these both elements, which spring 117 is coupled in corresponding recesses 118 in these elements. The spindle 95 and the spring 117 are protected against the interior of the brake caliper 1 by means of a bellows 119 which at its one side is fixed by means of a circlip or clamp ring 120 onto the housing support part 99 and at its other side in a groove 121 in the displacement block 112 without becoming loose.

For a better guidance and alignment of the sensor unit 91 so that the latter always runs in parallel to the rod 22 without tilting, the housing support part 99 is received by a mounting sleeve 122 which is inserted into the fixture opening 92 of the brake caliper 1.

It becomes apparent that the sensor unit 91 according to the invention can be mounted into the brake caliper 1 and removed therefrom in its entirety without the need to handle other components of the brake actuation mechanism 2 or to remove parts therefrom for the purpose of better accessibility. In order to exchange a defect sensor element 97 it is also not required to exchange the entire sensor unit, it is already sufficient to remove the housing fixture 96 from the housing support part 99.

The principle to detect the wear by means of the linear adjustment movement being performed by the thrust piece 4 allows use of a relatively simple and thus functionally reliable calculation circuit. Moreover, since no further components of the brake actuation mechanism 2 do influence the movement to be detected, the accuracy of the measurement can be increased.

What is claimed is:

1. A sensor device for the detection of the lining wear at a disc brake having a brake caliper and a brake actuation mechanism being arranged in the brake caliper, which comprises a thrust piece which cooperates directly or indirectly with a brake lining so that the movement of the brake lining corresponds to the movement of the thrust piece, wherein the sensor device can be inserted as a unit into an interior of the housing of the brake caliper from the rear and freely traverses the interior of the housing of the brake caliper up to the thrust piece, wherein the sensor device comprises a transmitting element for transmitting the linear movement of the thrust piece into a rotational movement and a sensor element for detecting the rotational movement, in which the transmitting element comprises a linear element attaching to the thrust piece which is displaceably arranged relative to a threaded element, which is stationary, but rotatably supported, in which the threaded element will be set into rotation upon displacement of the linear element and in which the threaded element at its end facing away from the brake disc cooperates with the sensor element in a touchless manner.

2. The sensor device of claim 1, wherein the sensor element is a Hall-sensor and interacts with at least one magnet being arranged at the end of the threaded element facing away from the brake disc.

3. The sensor device of claim 1, wherein the thread pitch of the threaded element is selected such that at maximum one entire turn is performed by the threaded element over the entire possible linear displacement of the linear element.

4. The sensor device of claim 1, wherein the linear element is biased in the axial direction.

5. A disc brake having a brake disc, a brake caliper and a brake actuation mechanism being arranged in the brake caliper, which comprises a thrust piece which cooperates directly or indirectly with a brake lining so that the movement of the brake lining corresponds to the movement of the thrust piece, comprising a sensor device for the detection of the lining wear, wherein the sensor device as a whole unit is inserted into an interior of the housing of the brake caliper from the rear, in parallel to the axis of the brake disc and outside of the brake actuation mechanism so as to freely traverse the interior of the housing of the brake caliper up to the thrust piece and to cooperate directly or indirectly with the thrust piece close by the brake lining, wherein the sensor device comprises a transmitting element for transmitting the linear movement of the thrust piece into a rotational movement for detecting the rotational movement and a sensor element for detecting the rotational movement, in which the transmitting element comprises a linear element being attached to the thrust piece, which linear element is displaceably arranged relative to a threaded element, which is stationary but rotatably supported, in which the threaded element will be set into rotation upon displacement of the linear element and in which the threaded element at its end facing away from the brake disc cooperates with the sensor element in a touchless manner.

6. The disc brake according to claim 5, wherein the sensor element is a Hall-sensor and interacts with at least one magnet being arranged at the end of the threaded element facing away from the brake disc.

7. The disc brake of claim 5, wherein the thread pitch of the threaded element is selected such that at maximum one entire turn is performed by the threaded element over the entire possible linear displacement of the linear element.

8. The disc brake of claim 5, wherein the linear element is biased in the axial direction.

9. A sensor device comprising a transmitting element for transmitting the linear movement of a thrust piece of a brake actuation mechanism of a disc brake into a rotational movement and a sensor element for detecting the rotational movement, wherein the transmitting element comprises a linear element to be attached to the thrust piece, which linear element is displaceably arranged relative to a threaded element, which is stationary but rotatably supported, in which the threaded element will be set into rotation upon displacement of the linear element and in which the threaded element at its end facing away from the brake disc cooperates with the sensor element in a touchless manner.

10. The sensor device of claim 9, wherein the sensor element is a Hall-sensor and interacts with at least one magnet being arranged at the end of the threaded element facing away from the brake disc.

11. The sensor device of claim 9, wherein the thread pitch of the threaded element is selected such that at maximum one entire turn is performed by the threaded element over the entire possible linear displacement of the linear element.

12. The sensor device of claim 9, wherein the linear element is biased in the axial direction.

* * * * *